United States Patent [19]

Clubley et al.

[11] Patent Number: 5,055,230
[45] Date of Patent: Oct. 8, 1991

[54] CORROSION INHIBITING COMPOSITIONS

[75] Inventors: Brian G. Clubley, Wilmslow; David C. Parker, Macclesfield, both of England

[73] Assignee: Ciba-Geigy Corporation, Ardsley, N.Y.

[21] Appl. No.: 524,675

[22] Filed: May 15, 1990

Related U.S. Application Data

[63] Continuation of Ser. No. 215,846, Jul. 6, 1988, abandoned.

[30] Foreign Application Priority Data

Jul. 14, 1987 [GB] United Kingdom ............... 8716586
Dec. 4, 1987 [GB] United Kingdom ............... 8728482

[51] Int. Cl.$^5$ .............................................. C23F 11/10
[52] U.S. Cl. ............................. 252/389.62; 252/396; 422/12; 422/13; 422/17; 549/274; 562/587; 260/413
[58] Field of Search ............... 252/396, 389.1, 389.62; 562/587; 260/413; 422/12, 13, 17; 549/274

[56] References Cited

U.S. PATENT DOCUMENTS

| | | | |
|---|---|---|---|
| 3,631,189 | 12/1971 | Snapp et al. | 562/587 |
| 3,952,016 | 4/1976 | Barillo et al. | 549/274 |
| 3,959,185 | 5/1976 | Barillo et al. | 512/12 |
| 3,989,637 | 11/1976 | Hogue et al. | 422/17 |
| 4,223,163 | 9/1980 | Guilloty | 562/587 |
| 4,419,258 | 12/1983 | Crutchfield | 562/587 |

FOREIGN PATENT DOCUMENTS

| | | |
|---|---|---|
| 0222311 | 5/1987 | European Pat. Off. |
| 456517 | 11/1936 | United Kingdom . |
| 807666 | 1/1959 | United Kingdom . |
| 1195652 | 8/1968 | United Kingdom . |
| 2088863A | 6/1982 | United Kingdom . |
| 2176783 | 1/1987 | United Kingdom . |

OTHER PUBLICATIONS

Chemical Abstracts, vol. 79, 1973, Abstract No. 18501e, Malinorskii, M. S. et al., "Reaction of α-Oxides with 2-Nitroethanol".
Chemical Abstracts, vol. 103, Abstract No. 1779975s, Nieuwenhuizen, et al., "Synthesis and Calcium Complexation of Polycarboxylic and Synthesis and Calcium Complexation of a Series of Low Molecular Weight Polycarboxylic Acids; Derivatives of Oxydiacetate and Ethylene Glycol Diacetate".
Chemical Abstracts, vol. 108, Abstract No. 37745w, S. M. Taderosyan et al., "Synthesis of 6-substituted-2-oxo-1,4-Dioxones".

*Primary Examiner*—Deborah L. Kyle
*Assistant Examiner*—Valerie D. Fee
*Attorney, Agent, or Firm*—Luther A. R. Hall

[57] ABSTRACT

A composition, in contact with a corrodable metal surface, comprising:

a) an aqueous-based or oil-based system; and
b) as an inhibitor for protecting the metal surface against corrosion, at least one compound having the formula I or II:

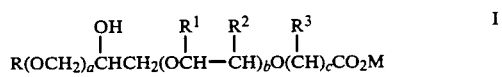

in which

R is $C_4$–$C_{20}$alkyl, $C_4$–$C_{20}$alkyl interrupted by one or more oxygen atoms, $C_4$–$C_{20}$alkenyl, $C_6$–$C_{10}$aryl, $C_7$–$C_{15}$alkaryl, $C_7$–$C_{15}$aralkyl or $C_5$–$C_{12}$cycloalkyl;

$R^1$, $R^2$ and $R^3$ are the same or different and each is methyl or, preferably, hydrogen;

M is hydrogen, a metal ion, ammonium or substituted ammonium ion;

a is 0 or 1;

b is 0 or an integer from 1 to 6, preferably 0, 1, 2 or 3 especially 0 or 1; and c is an integer from 1 to 6; and/or at least one compound having the formula II:

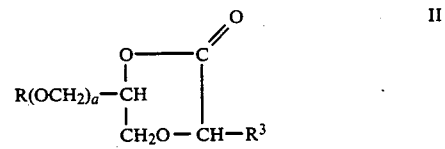

in which R, $R^3$ and a are as defined above.

19 Claims, No Drawings

CORROSION INHIBITING COMPOSITIONS

This application is a continuation of application Ser. No. 215,846, filed Jul. 6, 1988, now abandoned.

The present invention relates to corrosion inhibiting compositions.

Many formulations are known to inhibit the corrosion of ferrous metals in contact with aqueous or partially aqueous systems. Traditionally, such formulations contain, as corrosion inhibitor, a metal such as chromium or zinc, phosphorus in the form of phosphate, polyphosphate or phosphonate, or sodium nitrite. Most of these known corrosion inhibitors are now believed to have an adverse effect on the environment when they are discharged into natural water systems. These known corrosion inhibitors can cause environmental damage e.g. by their toxicity to fish, or by their tendency to promote biological growth.

There is therefore a need for environmentally-safe corrosion inhibitors.

We have now found certain hydroxy ether-acids, and related lactone compounds which show excellent ferrous corrosion inhibition, without the need for their co-use with toxic heavy metals or phosphorus containing compounds.

Accordingly, the present invention provides a composition in contact with a corrodable metal surface, preferably a ferrous metal surface, which composition comprises:

a) an aqueous-based or oil-based system; and b) as an inhibitor for protecting the metal surface against corrosion, at least one compound having the formula I or II:

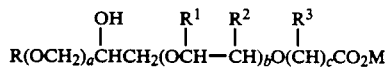

in which

R is $C_4$-$C_{20}$alkyl, $C_4$-$C_{20}$alkyl interrupted by one or more oxygen atoms, $C_4$-$C_{20}$alkenyl, $C_6$-$C_{10}$aryl, $C_7$-$C_{15}$alkaryl, $C_7$-$C_{15}$aralkyl or $C_5$-$C_{12}$cycloalkyl;

$R^1$, $R^2$ and $R^3$ are the same or different and each is methyl or, preferably, hydrogen;

M is hydrogen, a metal ion, ammonium or substituted ammonium ion;

a is 0 or 1;

b is 0 or an integer from 1 to 6, preferably 0, 1, 2 or 3 especially 0 or 1; and c is an integer from 1 to 6, preferably 1, 2 or 3.

It will be appreciated that, for those compounds of formula I in which b is 0, c is 1 and M is H, cyclisation is possible to form compounds having the formula II:

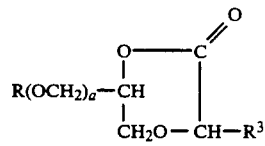

in which R, $R^3$ and a have their previous significance.

The corrosion inhibitor component of the compositions of the invention may be a mixture of one or more compounds of formula I with one or more compounds of formula II; or a mixture of compounds of formula I (or II) in which one substituent e.g. R varies from one compound of formula I (or II) to the next or in which b and/or c can be an average value representing a broad range of mixtures. Alternatively, the corrosion inhibitor component can be any mixture of pure enantiomers of formula I or II.

When, in the compounds of formula I or II, R is $C_4$-$C_{20}$alkyl it may be e.g. butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, or eicosyl; preferred alkyl groups R are those of straight chain, more preferably those having 6-16, especially 8-15 carbon atoms, most especially 12-15 carbon atoms.

When R is $C_4$-$C_{20}$alkyl interrupted by one or more oxygen atoms, it may be, for example, ethoxyethyl, ethoxybutyl, ethoxyoctyl, ethoxydecyl, ethoxyundecyl, ethoxydodecyl, ethoxytridecyl, ethoxyhexadecyl, ethoxyoctadecyl, diethoxyoctyl, diethoxynonyl, diethoxydecyl, diethoxyundecyl, diethoxydodecyl, diethoxytridecyl or diethoxyhexadecyl.

When R is $C_4$-$C_{20}$alkenyl, it may be butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl or eicosenyl.

$C_6$-$C_{10}$Aryl groups are phenyl or naphthyl groups.

$C_7$-$C_{15}$Alkaryl groups R include tolyl, ethylphenyl, butylphenyl, hexylphenyl, octylphenyl and nonylphenyl groups.

$C_7$-$C_{13}$Aralkyl groups R include benzyl, naphthylmethyl, α-methylbenzyl and α,α-dimethylbenzyl groups.

Examples of groups M in the compounds of formula I include hydrogen; alkali metal atoms such as sodium and potassium; alkaline earth metal atoms such as magnesium and calcium; ammonium; and substituted ammonium such as bis(2-hydroxyethyl) ammonium, tris(2-hydroxyethyl) ammonium, and bis(2-hydroxyethyl)-(2-hydroxy-3-p-nonylphenoxy)propyl ammonium.

Other useful substituted ammonium salts are those derived from commercially available amines, for example the commercially-available products "Primenes", "Armeens" and iso-nonyloxypropylamine.

Preferred compounds of formula I are those wherein R is $C_6$-$C_{15}$alkyl, a is 0 or 1, b is 0, 1, 2 or 3 and c is 1, 2 or 3; more preferred are those compounds of formula I wherein R is $C_8$-$C_{15}$alkyl, a is 0 or 1, b is 0 or 1 and c is 1, 2 or 3; more especially preferred compounds are those wherein R is $C_{12}$-$C_{15}$alkyl, a is 1, b is 0 and c is 1.

Preferred compounds of formula II are those wherein R is straight chain $C_6$-$C_{16}$alkyl, especially $C_8$-$C_{15}$alkyl and more especially $C_{12}$-$C_{15}$alkyl.

Most of the compounds of formula I or II are new and, as such, those new compounds form a further aspect of the present invention.

Some of the compounds of formula I, however, have been described previously. In particular, compounds of formula I in which R is $C_6$-$C_9$-alkyl, a is 0 or 1, b is 0, c is 1 and M is hydrogen or sodium, and compounds of formula II in which R is $C_6$-$C_9$alkyl and a is 0 or 1 have been disclosed in U.S. Pat. No. 3,952,016. The utility ascribed to these known compounds is as fragrances or flavoring agents. Moreover, in German Patent Specification DE 36 18 725-A there are described inter alia compounds of formula I of the present invention in which R is $C_4$-$C_{20}$alkyl or alkenyl and a is 1, b is 0 and c is 1. These compounds are said to be useful as anionic surfactants e.g. for cosmetics.

Accordingly, the present invention also provides compounds having the formula IA or IIA:

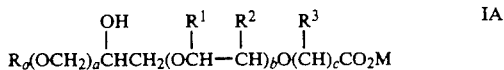

in which $R_o$ is $C_{10}$-$C_{20}$alkyl interrupted by one or more oxygen atoms, $C_4$-$C_{20}$alkenyl, $C_6$-$C_{10}$aryl, $C_7$-$C_{15}$alkaryl, $C_7$-$C_{15}$aralkyl or $C_5$-$C_{12}$cycloalkyl and $R^1$, $R^2$, $R^3$, M, a, b and c have their previous significance provided that $R_o$ is not $C_4$-$C_{20}$alkyl or $C_4$-$C_{20}$alkenyl when a is 1, b is 0 and c is 1 and $R^3$ is H.

It will be appreciated that for those compounds of formula IA in which b is 0, c is 1 and M is H, cyclisation is possible to form lactone compounds of formula IIA:

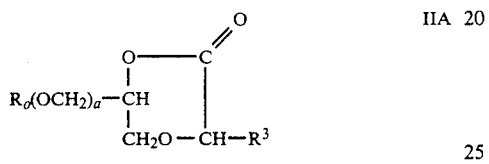

in which $R^3$ is not H, and $R_o$ and a have their previous significance.

The present invention provides a process for the production of a compound of formula I or II or IA or IIA by oxidising a compound of formula III:

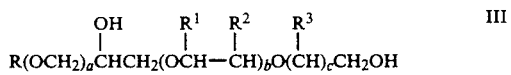

in which R, $R^1$, $R^2$, $R^3$, a, b and c have their previous significance, to give a compound of formula I, II, IA or IIA respectively.

The process according to the invention may use any conventional chemical oxidant. Preferred oxidants, however, are air or oxygen, optionally in the presence of a metal catalyst e.g. platinum or palladium, which may be supported on a suitable carrier. Other preferred oxidants are, for example, sodium hypohalites, optionally in conjunction with a catalyst.

Non-limiting examples of such catalysts are nitroxyl radicals such as tetramethylpiperidinyl nitroxyl radical.

The starting material of formula III may be produced e.g. by reacting an epoxide having the formula IV:

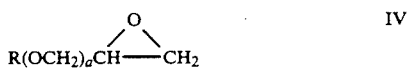

in which R and a have their previous significance, with an alcohol having the formula V:

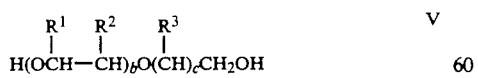

in which $R^1$, $R^2$, $R^3$, b and c have their previous significance.

The reaction between compounds of formula IV and V is optionally performed in the presence of a catalyst e.g. sodium metal, an amine or an ion-exchange resin.

When compounds of formula III in which b is 0 and c is 1 are oxidised according to the process of the present invention, compounds of formula I are produced which may be cyclised to the corresponding compounds of formula II, by methods well-known per se. Conversely, when a compound of formula II is produced by the process of the invention, such product of formula II may be converted into the corresponding compounds of formula I, especially a metal salt thereof, by methods well-known per se.

An alternative process for the preparation of compounds I or II comprises reacting a diol of formula VI:

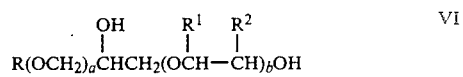

in which R, a, b, $R^1$ and $R^2$ have their previous significance, with a ω-halocarboxylic ester of formula VII:

wherein $R^3$ and c have the previous significance, X is halogen and $R^4$ is a hydrocarbon residue, preferably methyl or ethyl, in the presence of a suitable reagent such as sodium. This procedure provides compounds of formula VIII:

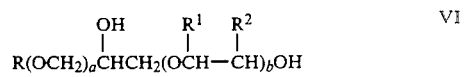

which can be hydrolysed to products of formula I and II by any of the methods known to those skilled in the art.

Yet another process for production of compounds of formula I and II comprises reacting a diol of formula VI with halo acid or salt of formula IX:

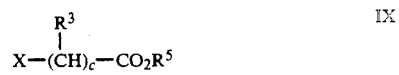

in which X, $R^3$ and c have their previous significance and $R^5$ is H or a metal ion with an appropriate amount of a base, e.g. sodium hydroxide. This procedure produces compounds of formula I and II directly.

When compounds of formula VI are reacted with compounds of formula VII and IX, reaction can also occur on the secondary alcohol to produce compounds of formula X and XI respectively:

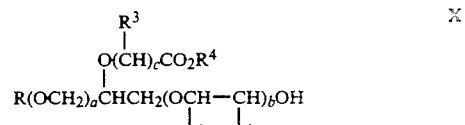

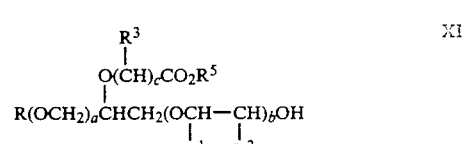

wherein R, $R^1$, $R^2$, $R^3$, $R^4$, $R^5$, a, b and c have their previous significance.

Compounds of formula X can be converted into compounds of formula XI by hydrolysis methods well known per se. Depending on the conditions chosen for the reactions between IV and VII or IX, the products produced can be varying mixtures of I and XI. These mixtures are also useful as corrosion inhibitors and, as such, form part of this invention.

A further process for producing compounds of formula I and II in which $R^3 = H$ and $c = 2$ comprises reacting diol of formula VI with acrylic acid or its sodium salt in the presence of an appropriate amount of a base such as sodium hydroxide for example. Again this method produces compounds of formula I directly.

Specific but non limiting examples of compounds of formula (I) of this invention are:

Where $R^3 = H$, $a = b = 0$, $c = 1$ 2-(2'-hydroxy)hexyloxyacetic acid
2-(2'-hydroxy)octyloxyacetic acid
2-(2'-hydroxy)decyloxyacetic acid
2-(2'-hydroxy)dodecyloxyacetic acid
2-(2'-hydroxy)hexadecyloxyacetic acid Where $R^3 = H$, $a = 1$, $b = 0$, $c = 1$ 2-(3'-butyloxy-2'-hydroxy)propoxyacetic acid
2-(3'-octyloxy-2'-hydroxy)propoxyacetic acid
2-(3'-decyloxy-2'-hydroxy)propoxyacetic acid
2-(3'-undecyloxy-2'-hydroxy)propoxyacetic acid
2-(3'-dodecyloxy-2'-hydroxy)propoxyacetic acid
2-(3'-tridecyloxy-2'-hydroxy)propoxyacetic acid
2-(3'-tetradecyloxy-2'-hydroxy)propoxyacetic acid
2-(3'-pentadecyloxy-2'-hydroxy)propoxyacetic acid
2-(3'-hexadecyloxy-2'-hydroxy)propoxyacetic acid Where $R^3 = H$, $a = b = 0$, $c = 2$ 3-(2'-hydroxy)hexyloxypropanoic acid
3-(2'-hydroxy)-decyloxypropanoic acid
3-(2'-hydroxy)-dodecyloxypropanoic acid Where $R^3 = H$, $a = 1$, $b = 0$, $c = 2$ 3-(3'-butyloxy-2'-hydroxy)propoxypropanoic acid
3-(3'-decyloxy-2'-hydroxy)propoxypropanoic acid
3-(3'-dodecyloxy-2'-hydroxy)propoxypropanoic acid Where $R^3 = H$, $a = b = 0$, $c = 3$ 4-(2'-hydroxy)octyloxybutanoic acid
4-(2'-hydroxy)decyloxybutanoic acid Where $R^3 = H$, $a = 1$, $b = 0$, $c = 3$ 4-(3'-octyloxy-2'-hydroxy)propoxybutanoic acid
4-(3'-decyloxy-2'-hydroxy)propoxybutanoic acid Where $R^3 = H$, $a = b = 0$, $c = 4$ 5-(3'-decyloxy-2'-hydroxy)propoxypentanoic acid Where $R^3 = H$, $a = b = 0$, $c = 5$ 6-(2'-hydroxy)decyloxyhexanoic acid Where $R^3 = H$, $a = 1$, $b = 0$, $c = 5$ 6-(3'-decyloxy-2'-hydroxy)propoxyhexanoic acid Where $R^3 = H$, $a = b = 0$, $c = 6$ 6-(2'-hydroxy)decyloxyheptanoic acid Where $R^3 = H$, $a = 1$, $b = 0$, $c = 6$ 7-(3'-decyloxy-2'-hydroxy)propoxyhexanoic acid Where $R^1 = R^2 = R^3 = H$, $a = 0$, $b = 1$ to $3$, $c = 1$ $C_{10}H_{21}CH(OH)CH_2(OCH_2CH_2)OCH_2CO_2H$
$C_{10}H_{21}CH(OH)CH_2(OCH_2CH_2)_2OCH_2CO_2H$
$C_{10}H_{21}CH(OH)CH_2(OCH_2CH_2)_3OCH_2CO_2H$ Where $R^1 = R^2 = R^3 = H$, $a = 1$, $b = 1$ to $3$, $c = 1$ $C_{10}H_{21}OCH_2CH(OH)CH_2(OCH_2CH_2)OCH_2CO_2H$
$C_{10}H_{21}OCH_2CH(OH)CH_2(OCH_2CH_2)_2OCH_2CO_2H$
$C_{10}H_{21}OCH_2CH(OH)CH_2(OCH_2CH_2)_3OCH_2CO_2H$ as well as the corresponding metal e.g. sodium, and the amine e.g. triethanolamine salts of the acids.

Specific but not limiting examples of compounds of formula (II) of this invention are:

Where $R^3 = H$, $a = 0$

6-Butyl-1,4-dioxan-2-one
6-Octyl-1,4-dioxan-2-one
6-Decyl-1,4-dioxan-2-one
6-Undecyl-1,4-dioxan-2-one
6-Dodecyl-1,4-dioxan-2-one
6-Tridecyl-1,4-dioxan-2-one
6-Tetradecyl-1,4-dioxan-2-one
6-Pentadecyl-1,4-dioxan-2-one
6-Hexadecyl-1,4-dioxan-2-one
6-Eicosyl-1,4-dioxan-2-one Where $R^3 = H$, $a = 1$ 6-Butoxymethyl-1,4-dioxan-2-one
6-Octyloxymethyl-1,4-dioxan-2-one
6-Decyloxymethyl-1,4-dioxan-2-one
6-Dodecyloxymethyl-1,4-dioxan-2-one
6-Undecyloxymethyl-1,4-dioxan-2-one
6-Tridecyloxymethyl-1,4-dioxan-2-one
6-Tetradecyloxymethyl-1,4-dioxan-2-one
6-Pentadecyloxymethyl-1,4-dioxan-2-one
6-Hexadecyloxymethyl-1,4-dioxan-2-one
6-Eicosoyloxymethyl-1,4-dioxan-2-one Any amount of the compound of formula I or II or mixture thereof, which is effective as a corrosion inhibitor in the composition according to the invention can be used, but the amount preferably ranges from 0.0001 to 5% by weight, based on the total weight of the aqueous- or oil-based system.

The substrate base for the composition of the present invention is either a) an aqueous-based system or b) an oil-based system. The substrate base is preferably an aqueous-based system.

Examples of systems which may provide the base for the compositions according to the present invention include functional fluids such as oils for technical use, lubricants e.g. those having a mineral oil, poly-alpha olefin or synthetic carboxylic acid ester base or mixtures thereof; hydraulic fluids e.g. those based on mineral oils, phosphate esters, aqueous polyglycol/polyglycol ether mixtures or glycol systems; oil-in-water or water-in-oil-systems; metal-working fluids having, as their base, mineral oil or aqueous systems; water- or aqueous glycol- or ethylene or propylene glycol/methanol based engine coolant systems; transformer- or switch oils; as well as aqueous systems e.g. industrial cooling water; aqueous air-conditioning systems; steam-generating systems; sea-water evaporator systems; hydrostatic cookers; and aqueous closed circuit heating or refrigerant systems.

When a functional fluid system is a synthetic lubricant, examples thereof include lubricants based on a diester of a dibasic acid and a monohydric alcohol, for instance dioctyl sebacate or dinonyladipate; on a triester of trimethylolpropane and a monobasic acid or mixture of such acids, for instance trimethylol propane tripelargonate, trimethylolpropane tricaprylate or mixtures thereof; on a tetraester of pentaerythritol and a monobasic acid or mixture of such acids, for instance pentaerythritol tetracaprylate; or on complex esters derived from monobasic acids, dibasic acids and polyhydric alcohols, for instance a complex ester derived from trimethylol propane, caprylic acid and sebacic acid; or on mixtures thereof.

Other lubricants are those known to the art-skilled and described e.g. in Schewe-Kobek, "Schmiermittel-Taschenbuch" (Huethig Verlag, Heidelberg 1974) and D. Klamann "Schmierstoffe und verwandte Produkte", Verlag Chemie, Weinheim 1982. Especially suitable appart from the preferred mineral oils are e.g. phosphates, glycols, polyglycols, polyalkylene glycols and poly-alpha olefins.

In order to improve various applicational properties, a functional fluid composition of the invention may also contain other additives such as, for oil-based systems, one or more of antioxidants, metal deactivators, further corrosion or rust inhibitors, viscosity-index improvers, pour-point depressants, dispersants/surfactants or antiwear additives; and for aqueous-based systems, one or more of antioxidants, other corrosion- and rust inhibitors, metal deactivators, complexing agents, precipitation inhibitors, biocides, buffering agents and antifoams.

For oil-based systems, examples of other additives are:

EXAMPLES OF PHENOLIC ANTIOXIDANTS

1. Alkylated Monophenols 2,6-Di-tert-butyl-4-methylphenol, 2,6-di-tert-butylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-di-cyclcopentyl-4-methylphenol, 2-(β-methylcyclohexyl)-4,6-dimethylphenol, 2,6-di-octa-decyl-4-methylphenol, 2,4,6-tricyclohexylphenol, 2,6-di-tert-butyl-4-methoxymethylphenol, o-tert-butylphenol.

2. Alkylated Hydroquinones 2,6-Di-tert-butyl-4-methoxyphenol, 2,5-di-tert-butylhydroquinone, 2,5-di-tert-amyl-hydroquinone, 2,6-diphenyl-4-octadecyloxyphenol.

3. Hydroxylated Thiodiphenylethers 2,2'-Thio-bis-(6-tert-butyl-4-methylphenol), 2,2'-thio-bis-(4-octyl-phenol), 4,4'-thio-bis-(6-tert-butyl-3-methyphenol), 4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl)-phenol), 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-(6-(α-methylbenzyl-4-nonylphenol), 2,2'-methylene-bis-(6-(α,α-dimethylbenzyl)-4-nonylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)-butane, 2,6-di-(3-tert-butyl-5-methyl-2-hydroxybenzyl)-4-methylphenol, 1,1,3-tris-(5-tert-butyl-4-hydroxy-2-methylphenyl)-3-n-dodecyl)-mercaptobutane, ethyleneglycolbis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis-(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethylbenzyl)dithiolterephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols

4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-di-tert-butyl-4-hydroxyphenol)-propionic acid with mono- or polyhydric alcohols, for example with methanol, diethyleneglycol, octadecanol, triethyleneglycol, 1,6-hexanediol, pentaerythritol, neopentylglycol, tris-hydroxyethyl-isocyanurate, thiodiethyleneglycol, bis-hydroxyethyl-oxalic acid diamide.

8. Esters of β-(5-tert-butyl-4-hydroxy-3-methylphenyl)-propionic acid with mono- or polyhydric alcohols, for example with methanol, diethyleneglycol, octadecanol, triethyleneglycol, 1,6-hexanediol, pentaerythritol, neopentylglycol, tris-hydroxyethyl-isocyanurate, thiodiethyleneglycol, di-hydroxyethyl-oxalic acid diamide.

9. Amides of β-(3,5-di-tert-butyl-4-hydroxyphenyl)-propionic acid for example

N,N'-Bis-(3,5-di-tert-butyl-4-hydroxyphenylpropionyl)-hexamethylenediamine, N,N'-bis-(3,5-di-tert-butyl-4-hydroxyphenylpropionyl)-trimethylene-diamine, N,N'-bis-(3,5-di-tert-butyl-4-hydroxyphenylpropionyl)-hydrazine.

Examples of amine antioxidants:

N,N'-Di-isopropyl-p-phenylenediamine, N,N'-di-sec.-butyl-p-phenylenediamine, N,N'-bis(1,4-dimethylpentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluene-sulfonamido)diphenylamine, N,N'-dimethyl-N,N'-di-sec-butyl-p-phenylenediamine, diphenylamine, N-allyldiphenylamine, 4-isopropoxy-diphenylamine, N-phenyl- 1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoylamino-phenol, 4-octadecanoylamino-phenol, di-(4-methoxy-phenyl)-amine, 2,6-di-tert-butyl-4-dimethylamino-methyl-phenol, 2,4'-diamino-diphenylmethane, 4,4'-diamino-diphenylmethane, N,N,N',N'-tetramethyl-4,4'-diamino-diphenylmethane, 1,2-di-(phenylamino)-ethane, 1,2-di-[2-methyl-phenyl)amino]-ethane, 1,3-di-(phenylamino)-propane, (o-tolyl)-biguanide, di-[4-(1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, n-allylphenothiazine.

Examples for other antioxidants

Aliphatic or aromatic phosphites, esters of thiodipropionic acid or of thiodiacetic acid, or salts of dithiocarbamic or dithiophosphoric acid.

Examples of metal deactivators, for example for copper, are:

Triazoles, benzotriazoles and derivatives thereof, tolutriazole and derivatives thereof, 2-mercaptobenzothiazole, 2-mercaptobenzotriazole, 2,5-dimercaptothiadiazole, 2,5-dimercaptobenzotriazole, 5,5'-methylene-bis-benzotriazole, 4,5,6,7-tetrahydrobenzotriazole, salicylidene-propylenediamine and salicylaminoguanidine and salts thereof.

Examples of rust inhibitors are:

a) Organic acids, their esters, metal salts and anhydrides, e.g. N-oleoyl-sarcosine, sorbitan-mono-oleate, lead-naphthenate, alkenylsuccinic acids and -anhydrides, e.g. dodecenyl-succinic acid anhydride, succinic acid partial esters and amides, 4-nonyl-phenoxy-acetic acid.

b) Nitrogen-containing compounds, e.g.

I. Primary, secondary or tertiary aliphatic or cycloaliphatic amines and amine-salts of organic and inorganic acids, e.g. oil-soluble alkylammonium carboxylates II. Heterocyclic compounds, e.g., substituted imidazolines and oxazolines.

c) Phosphorus-containing compounds, e.g., Amine salts of phosphonic acid or phosphoric acid partial esters, zinc dialkyldithio phosphates.

d) Sulfur-containing compounds, e.g., Barium-dinonylnaphthalene-n-sulfonates, calcium petroleum sulfonates.

Examples of viscosity-index improvers are:

Polyacrylates, polymethacrylates, vinylpyrrolidone/methacrylate-copolymers, polyvinylpyrrolidones, polybutenes, olefin-copolymers, styrene/acrylate-copolymers, polyethers.

Examples of pour-point depressants are:

Polymethacrylates, alkylated naphthalene derivatives.

Examples of dispersants/surfactants are:

Polybutenylsuccinic acid-amides or -imides, polybutenylphosphonic acid derivatives, basic magnesium-, calcium-, and bariumsulfonates and -phenolates.

Examples of anti-wear additives are:

Sulfur- and/or phosphorus- and/or halogen-containing compounds e.g. sulfurised vegetable oils, zinc dialkyldithiophosphates, tritolylphosphate, chlorinated paraffins, alkyl- and aryldi- and trisulfides, triphenylphosphorothionate, diethanolaminomethyltolutriazole, di(2-ethylhexyl)-aminomethyltolutriazole.

In the treatment of substrates which are completely aqueous, such as cooling water systems, air-conditioning systems, steam-generating systems, sea-water evaporator systems, hydrostatic cookers, and closed circuit heating or refrigerant systems, further corrosion inhibitors may be used such as, for example, water soluble zinc salts; phosphates; polyphosphates; phosphonic acids and their salts, for example, hydroxyethyldiphosphonic acid (HEDP), nitrilotris methylene phosphonic acid and methylamino dimethylene phosphonocarboxylic acids and their salts, for example, those described in German Offenlegungsschrift 26 32 774, hydroxyphosphonoacetic acid, 2-phosphonobutane-1,2,4-tricarboxylic acid and those disclosed in GB 1 572 406; nitrates, for example sodium nitrate; nitrites e.g. sodium nitrite; molybdates e.g. sodium molybdate; tungstates; silicates e.g. sodium silicate; benzotriazole, bis-benzotriazole or copper deactivating benzotriazole or tolutriazole derivatives or their Mannich base derivatives; mercaptobenzothiazole; N-acyl sarcosines; N-acylimino diacetic acids; ethanolamines; fatty amines; and polycarboxylic acids, for example, polymaleic acid and polyacrylic acid, as well as their respective alkali metal salts, copolymers of maleic anhydride, e.g. copolymers of maleic anhydride and sulfonated styrene, copolymers of acrylic acid e.g. copolymers of acrylic acid and hydroxyalkylated acrylic acid, and substituted derivatives of polymaleic and polyacrylic acids and their copolymers. Moreover, in such completely aqueous systems, the corrosion inhibitor used according to the invention may be used in conjunction with dispersing and/or threshold agents e.g. polymerised acrylic acid (or its salts), phosphinopolycarboxylic acids (as described and claimed in British Patent 1 458 235), the cotelomeric compounds described in European Patent Application No. 1 050 706, hydrolysed polyacrylonitrile, polymerised methacrylic acid and its salts, polyacrylamide and co-polymers thereof from acrylic and methacrylic acids, lignin sulphonic acid and its salts, tannin, naphthalene sulphonic acid/formaldehyde condensation products, starch and its derivatives, cellulose, acrylic acid/lower alkyl hydroxyacrylate copolymers e.g. those described in U.S. Pat. No. 4,029,577, styrene/maleic anhydride copolymers and sulfonated styrene homopolymers e.g. those described in U.S. Pat. No. 4,374,733 and combinations thereof. Specific threshold agents, such as for example, 2-phosphonobutane-1,2,4-tri-carboxylic acid (PBSAM), hydroxyethyldiphosphonic acid (HEDP), hydrolysed polymaleic anhydride and its salts, alkyl phosphonic acid, hydroxyphosphonoacetic acid 1-aminoalkyl-1, 1-diphosphonic acids and their salts, and alkali metal poly-phosphates, may also be used.

Particularly interesting additive packages are those comprising compounds of formula I with one or more of polymaleic acid or polyacrylic acid or their copolymers, or substituted co-polymers, HEDP, PBSAM, hydroxyphosphonoacetic acid, triazoles such as tolutriazole, molybdates and nitrites, zinc, benzoic acid, phosphates and s-triazine derivatives.

Precipitating agents such as alkali metal orthophosphates, carbonates; oxygen scavengers such as alkali metal sulphites and hydrazines; sequestering agents such as nitrilotriacetic acid and its salts; anti-foaming agents such as silicones e.g. polydimethylsiloxanes, distearylsebacamides, distearyladipamide and related products derived from ethylene oxide and/or propylene oxide condensations, in addition to fatty alcohols, such as capryl alcohols and their ethylene oxide condensates;

and biocides e.g. amines, quaternary ammonium compounds, chlorophenols, sulphur-containing compounds such as sulphones, methylene bis thiocyanates and carbamates, isothiazolones, brominated propionamides, triazines, phosphonium compounds, chlorine and chlorine-release agents and organometallic compounds such as tributyl tin oxide, may be used.

The functional fluid system may be partly aqueous e.g. an aqueous machining fluid formulation, e.g. a water dilutable cutting or grinding fluid.

The aqueous machining fluid formulations according to the invention may be e.g. metal working formulations. By "metal working" we mean reaming, broaching, drawing, spinning, cutting, grinding, boring, milling, turning, sawing, non-cutting shaping, rolling or quenching. Examples of water-dilutable cutting or grinding fluids into which the corrosion inhibiting compound may be incorporated include:

a) Aqueous concentrates of one or more corrosion inhibitors, and optionally one or more anti-wear additives which are usually employed as grinding fluids;

b) Polyglycols containing biocides, corrosion inhibitors and anti-wear additives for cutting operations or grinding;

c) Semi-synthetic cutting fluids similar to (b) but containing in addition 10 to 25% oil with sufficient emulsifier to render the water diluted product translucent;

d) An emulsifiable mineral oil concentrate containing, for example, emulsifiers, corrosion inhibitors, extreme pressure/anti-wear additives, biocides, antifoaming agents, coupling agents etc.; they are generally diluted with water to a white opaque emulsion;

e) A product similar to (d) containing less oil and more emulsifier which on dilution gives a translucent emulsion for cutting or grinding operations.

For those partly-aqueous systems in which the functional fluid is an aqueous machining fluid formualtion the inhibitor component b) may be used singly, or in admixture with other additives e.g. known further corrosion inhibitors or extreme-pressure additives.

Examples of other corrosion inhibitors which may be used in these partly aqueous systems, in addition to the compound of formula I used according to the invention, include the following groups:

a) Organic acids, their esters or ammonium, amine, alkanolamine and metal salts, for example, benzoic acid, p-tert-butyl benzoic acid, disodium sebacate, triethanolamine laurate, iso-nonanoic acid, triethanolamine salt of p-toluene sulphonamido caproic acid, triethanolamine salt of benzene sulphonamide caproic acid, triethanolamine salts of 5-ketocarboxylic acid derivatives as described in European Patent No. 41 927, sodium N-lauroyl sarcosinate or nonyl phenoxy acetic acid;

b) Nitrogen containing materials such as the following types: fatty acid alkanolamides; imidazolines, for example, 1-hydroxy-ethyl-2-oleylimidazolines; oxazolines; triazoles for example, benzotriazoles; or their Mannich base derivatives; triethanolamines; fatty amines; inorganic salts, for example, sodium nitrate; and the carboxy-triazine compounds described in European Patent No. 46 139;

c) Phosphorus containing materials such as the following types: amine phosphates, phosphonic acids or inorganic salts, for example, sodium dihydrogen phosphate or zinc phosphate;

d) Sulphur containing compounds such as the following types: sodium, calcium or barium petroleum sulphonates, or heterocyclics, for example, sodium mercaptobenzothiazole. Nitrogen containing materials, particularly triethanolamine, are preferred.

The following Examples further illustrate the present invention.

Certain of the following Examples describe the production of lactones of formula II as hereinbefore defined. These lactones can be converted readily into the corresponding compound of formula I as hereinbefore defined by dissolution in water and adjustment of the pH of the resulting solution to a value of 7 or above.

EXAMPLE 1

6-Decyl-1,4-dioxan-2-one

Sodium (0.25 moles) is stirred in 150 ml of dry toluene and dodecane-1,2-diol (0.25) is added dropwise at 40° C. When addition is complete, the mixture is heated at reflux to dissolve the sodium. After cooling to room temperature, ethyl chloroacetate (0.32 moles) is added over 10 minutes.

The mixture is now refluxed for 12 hours, during which time a white precipitate is produced. After cooling, equal volumes of water and petroleum ether are added and the resultant mixture allowed to separate.

The organic layer is evaporated to dryness. The residue is taken up in petroleum ether and the white solid filtered off and discarded. Again the solvent is evaporated.

The residue is refluxed with 850 ml water containing 60 g of sodium hydroxide for 18 hours, before cooling and washing with a mixture of ether and petroleum spirit. The aqueous layer is then acidified to pH 1.5 using 98% sulphuric acid. The product is taken up into 1000 ml of ether. After drying, the solvent is evaporated to yield 33% of the title compound which has satisfactory spectral properties (i.r. and n.m.r.).

EXAMPLES 2 TO 6

Using the method of Example 1 above, the following compounds are also synthesized;

EXAMPLE 2

6-Butyl-1,4-dioxan-2-one

EXAMPLE 3

6-Hexyl-1,4-dioxan-2-one

EXAMPLE 4

6-Butoxymethyl-1,4-dioxan-2-one

EXAMPLE 5

6-Isooctylmethyl-1,4-dioxan-2-one

EXAMPLE 6

6-Phenoxymethyl-1,4-dioxan-2-one

All isolated compounds having satisfactory spectral details (i.r. and n.m.r.).

EXAMPLES 7 TO 11

The same method of Example 1 is again employed but replacing the ethyl chloroacetate with ethylchloropropionate to prepare

EXAMPLE 7

3-(2'-hydroxy)octyloxypropanoic acid

EXAMPLE 8

3-(2'-hydroxy)decyloxypropanoic acid

EXAMPLE 9

3-(2'-hydroxy)dodecyloxypropanoic acid

EXAMPLE 10

3-(3'-isooctyloxy-2'-hydroxy)propoxypropanoic acid

Again all isolated compounds having satisfactory spectral details.

EXAMPLE 11

6-Octyl-1,4-dioxan-2-one

Powdered decane-1,2-diol (0.25 moles) is stirred at room temperature and very well powdered sodium hydroxide (0.25 moles) is added in portions. Gentle heating of the mixture to 55° C. gives a viscous yellow paste. Sodium chloroacetate (0.25 moles) is now added in portions over 10 minutes. The white mobile paste produced is stirred at 70°-60° C. for 1.75 h. After cooling to 20° C., 100 ml of petroleum ether is added followed by water. After separation of phases (aided by acetone) the aqueous phase is run off and acidified to pH 1.5 using 98% sulphuric acid. The oil produced is taken up into 2×375 ml diethyl ether which is then dried and evaporated to leave the title product as a clear oil (63%).

EXAMPLE 12

6-Decyl-1,4-dioxan-2-one

Sodium (0.08 moles) is added in small pieces to ethylene glycol (dried over 4A mol. sieves-7.2 moles) and the mixture heated to 130° C. After complete solution of the sodium, dodecene-1,2-oxide (0.66 moles) is added over 15 minutes. After a further 1 hour at 130° C. the mixture is heated at 150° C. for 18 hours.

Excess ethylene glycol is removed in vacuo (water pump). The resultant residue is dissolved in 600 ml dichloromethane and washed with water. The organic phase is dried and evaporated.

A portion of the resultant brown liquid (0.01 moles) is stirred in 50 ml water containing 5 ml dioxan and 0.02 moles of sodium hydroxide, together with 0.5 g of a 5% platinum on charcoal catalyst. Air is forced over the reaction mixture, which is heated at 70° C. for 12 hours.

The catalyst is removed by filtration and the aqueous solution acidified. The product is extracted into ether which is dried and evaporated to yield the product as a brown oil which crystallises to a buff solid. Shaking the product with 60-80 petroleum ether, followed y filtration, gives the product as a white crystalline solid (m.p. 52°-52.5° C.) with satisfactory spectra (i.r., n.m.r.).

EXAMPLE 13

6-Decyloxymethyl-1,4-dioxan-2-one 43 g of ethylene glycol is stirred under nitrogen at 20° C. and 0.16 g of sodium added. The mixture is heated at 100° C. until all the sodium dissolves, at which time 15 g of decylglycidyl ether is added over 0.5 hours. The resulting mixture is then stirred at 130° C. for 17 hours before cooling and adding 0.4 g of glacial acetic acid. The excess ethylene glycol is next removed in vacuo (water pump) to leave a residue which is not isolated.

To this residue is added 200 ml of distilled water and the resulting inhomogeneous mixture heated to 70° C. and 0.8 g of catalyst (5% Pd on charcoal) added. Air is drawn over the reactants and the pH maintained between pH 10 and pH 10.5 by titrating amount of sodium hydroxide solution. When the reaction has consumed the theoretical amount of sodium hydroxide, it is cooled and filtered. After washing with ether the aqueous phase is acidified to pH 1.5 using 98% sulphuric acid. The oil produced is extracted into ether which is then dried and evaporated to leave the product as an oil (30%) which has satisfactory spectral properties (i.r., n.m.r.).

EXAMPLE 14

6-$C_9$-$C_{11}$Alkoxymethyl-1,4-dioxan-2-one

Using the method described in Example 13, a glycidyl ether derived from Linevol 911 (a mixed $C_9$-$C_{11}$alcohol sold by Shell) is reacted with ethylene glycol and the title product was obtained containing a small amount of lactone—in 64% yield with satisfactory spectral properties (i.r.+n.m.r.).

In this preparation the catalytic oxidation was performed using oxygen rather than air as in Example 13.

EXAMPLE 15

6-$C_{12}$-$C_{13}$Alkyloxymethyl-1,4-dioxan-2-one

Sodium (0.83 g) is dissolved in ethylene glycol (223.8 g) and the glycidyl ether derived from Dobanol 23 (a mixture of mainly linear $C_{12}$ and $C_{13}$ alcohols, produced by Shell) (90.0 g) is added dropwise over 1 hour at 130°-150° C. under an atmosphere of nitrogen. The mixture is then reacted at this temperature for 11 hours. Acetic acid (2.16 g) is added, after cooling, and the ethylene glycol is removed by distillation. The residue is purified by distillation under high vacuum.

50 g of the product so obtained is dissolved in 500 ml of dichloromethane, and 16 ml of a 0.1M solution of tetramethyl piperidyl nitroxyl radical in dichloromethane, together with 1.9 g of potassium bromide dissolved in 20 ml of water are added.

This mixture is stirred rapidly whilst 500 ml of a 7% solution of sodium hypochlorite, saturated with sodium bicarbonate, are added, dropwise, with cooling, such that the temperature remains below 5° C. After completion of the addition, the mixture is stirred for a further 10 minutes. Excess oxidant is decomposed with aqueous sodium sulphate, and the mixture is then acidified with a 7% HCl solution.

After separation of the phases, the organic phase is run off, washed with water and dried. Evaporation of the solvent in vacuo gives the title dioxan-2-one as an orange mobile liquid (mass recovery=96%).

$^1$H nmr: $\delta$=4.5 (1H,m) CHOCO, 4.2 (2H,s OCH$_2$CO), 4.0-3.2 (6H, m CH$_2$O) 1.7-0.9 (alkyl chain).

I.r.: 2900 cm$^{-1}$ (C—H), 1750 cm$^{-1}$ (C=O).

EXAMPLES 16–22

Using the method described in Example 15 and starting from the appropriate glycidyl ethers described below the following compounds are prepared.

EXAMPLE 16

6-Dodecyloxymethyl-1,4-dioxan-2-one

Prepared from the glycidyl ether of dodecanol.

EXAMPLE 17

6-Tridecyloxymethyl-1,4-dioxan-2-one

Prepared from the glycidyl ether of tridecanol.

EXAMPLE 18

6-Tetradecyloxymethyl-1,4-dioxan-2-one

Prepared from the glycidyl ether of tetradecanol.

EXAMPLE 19

6-Hexadecylmethyl-1,4-dioxan-2-one

Prepared from the glycidyl ether of hexadecanol.

EXAMPLE 20

6-$C_{14}$-$C_{15}$-alkyloxymethyl-1,4-dioxan-2-one

Prepared from the glycidyl ether of Dobanol 45, a mixture of $C_{14}$ and $C_{15}$ alcohols commercially available from Shell.

EXAMPLE 21

6-$C_{12}$-$C_{15}$-alkyloxymethyl-1,4-dioxan-2-one

Prepared from Azepoxy 8, a commercially available mixture of $C_{12}$ and $C_{14}$ glycidyl ethers supplied by the AZS corporation.

EXAMPLE 22

6-$C_{12}$-$C_{15}$-alkyloxymethyl-1,4-dioxan-2-one

Prepared from Epoxy 8, a commercially available mixture of $C_{12}$ and $C_{14}$ glycidyl ethers supplied by Proctor and Gamble.

EXAMPLE 23

3-(3′-alkoxy-2′-hydroxy)propoxy propanoic acid

Using the method of Example 14, but replacing ethylene glycol with 1,3-propane diol, the title product is obtained in 23% yield, again with satisfactory spectral properties (i.r.+n.n.r.).

EXAMPLE 24

4-(3′-alkoxy-2′-hydroxy)propoxybutanoic acid

Using the method of Example 14, but replacing ethylene glycol with 1,4-butone diol, the title product is obtained in good yield and with satisfactory spectral properties (i.r.+n.m.r.).

EXAMPLE 25

4-(3′-alkoxy-2′-hydroxy)propoxybutanoic acid-sodium salt

The final aqueous solution in Example 17, before acidification, is found—by drying—to be a 7.3% w/w solution of the title compound sodium salt.

EXAMPLE 26 AND 27

Using the procedures of Examples 13–14 and 24–25 the following compounds have also been synthesized

EXAMPLE 26

2-(3′-$C_9$-$C_{11}$alkoxy-2′-hydroxy)propoxyacetic acid, sodium salt

EXAMPLE 27

2-(3′-paranonylphenoxy-2′-hydroxy)propoxyacetic acid.

EXAMPLE 28

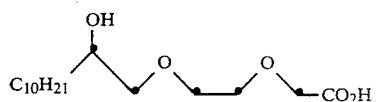

Using the same procedure as in Example 13, dodecene-1,2-oxide is reacted with diethylene glycol. In this case the intermediate product is distilled to give $C_{10}H_{21}CH(OH)CH_2OCH_2CH_2OCH_2CH_2OH$ as a white crystalline solid (b.p. 120° C./0.2 mm Hg). This diol is then oxidised as in Example 16 to produce the above compound in good yield with satisfactory spectral details (i.r.+n.m.r.) as a yellow oil.

EXAMPLE 29

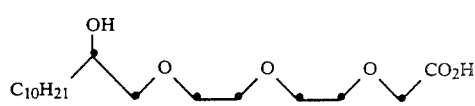

The title compound is prepared using the procedure described in Example 28, but replacing the diethylene glycol with triethyleneglycol.

EXAMPLE 30

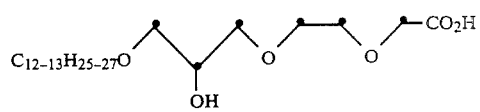

The title compound is prepared by the method of Example 21 using the glycidyl ether derived from Dobanol 23 (a mixed $C_{12}$-$C_{13}$alcohol from Shell).

EXAMPLE 31

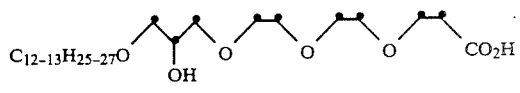

Using the method of Example 21, reacting the glycidyl ether derived from Dobanol 23 with triethylene glycol, the title compound is prepared. Dissolving the compounds of Examples 1–24 in sodium hydroxide solution gives rise to the sodium salts of the compounds.

EXAMPLE 32

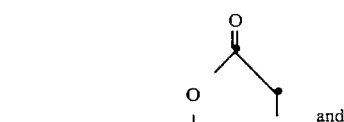

and

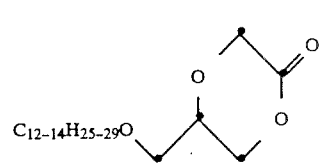

Azepoxy 8, (the glycidyl ether described in Example 21 above) (28 ml) is added dropwise over 15 minutes to 28 ml of 20% HCl at reflux under nitrogen. After addition is complete reflux is maintained for a further 15 minutes. The mixture is cooled and allowed to separate.

EXAMPLES 33 TO 36

Corrosion inhibitor activity of compounds of formula I or II is demonstrated in the Aerated Solution Bottle Test using standard corrosive waters have the following compositions:

|  | 2M | 5M | 8M |
|---|---|---|---|
| pH | 7.2 | 7.6 | 8.0 |
| pA | 0 | 0 | 0 |
| TA | 20 | 204 | 210 |
| TH | 110 | 216 | 580 |
| Ca (ppm) | 75 | 150 | 500 |
| Mg (ppm) | 35 | 66 | 80 |
| Cl$^-$ (ppm) | 5 | 36 | 300 |
| SO$_4^{2-}$ (ppm) | 110 | 40 | 40 |

In the Table, "pA" denotes phenol alkalinity in ppm as CaCO$_3$; "TA" denotes total alkalinity in ppm as CaCO$_3$; and "TH" denotes total hardness in ppm as CaCO$_3$.

Mild steel coupons measuring 5 cms by 2.5 cms are scrubbed with pumice, immersed for one minute in hydrochloric acid and then rinsed, dried and weighed.

200 ppm of test additive as a sodium salt is dissolved in 200 ml of standard corrosive water. Two steel coupons are suspended in the solution, and the whole stored in a closed bottle in a thermostat at 40° C. During the storage period, air is passed into the solution at 500 ml/minute, the passage of the air being screened from the steel coupon; any water losses by evaporation are replaced with distilled water.

After 64 hours, the steel coupons are removed, scrubbed without pumice, immersed for one minute in hydrochloric acid inhibited with 1% by weight of hexamine and then rinsed, dried and reweighed. A certain loss in weight will have occurred. A blank test i.e. immersion of mild steel specimen in the test water in the absence of any potential corrosion inhibitor, is carried out with each series of tests. The corrosion rates are calculated in milligrams of weight loss/sq. decimeter/day (m.d.d.).

The results obtained in a series of tests are set out in Table I.

TABLE I

| Example | Inhibitor (200 ppm) | Corrosion Rate (m.d.d.) | | |
|---|---|---|---|---|
| | | 2M | 5M | 8M |
| — | none (control) | 48.5 | 50.3 | 51.7 |
| 33 | Product Ex. 9 | 3.7 | 3.0 | 6.5 |
| 34 | Product Ex. 13 | 1.2 | 1.0 | 1.4 |
| 35 | Product Ex. 14 | 1.6 | 3.5 | 3.1 |
| 36 | Product Ex. 24 | 2.6 | 1.6 | 3.3 |

EXAMPLES 37 AND 42

The corrosion inhibitor activity of the product of Examples 14 and 15 is examined in the Rotating Coupon Test using the following standard corrosive waters:

|  | 50 Ca | 150 Ca |
|---|---|---|
| pH | 7.0 | 7.4 |
| pA | 0 | 0 |
| TA | 20 | 150 |
| TH | 75 | 225 |
| Ca2+ (ppm) | 50 | 150 |
| Mg2+ (ppm) | 25 | 75 |
| Cl$^-$ (ppm) | 20 | 60 |
| SO$_4^{2-}$ (ppm) | 20 | 50 |

In a 1 liter reservoir of one of the test waters, two-precleaned and pre-weighed mild steel coupons are rotated at a coupon velocity of 61 cms per second. The test is conducted over 48 hours in oxygenated water at 40° C. using 20 ppm of the appropriate concentration of corrosion inhibitor.

The coupons are removed, cleaned and the corrosion rates are determined as determined as described in Examples 33 to 36. The results are shown in Table II below:

TABLE II

| Example | Inhibitor | Inhibitor Concentration (ppm) | Corrosion rate (m.d.d.) in test water | |
|---|---|---|---|---|
| | | | 50 Ca | 150 Ca |
| — | none (control) | | 275.8 | 130.2 |
| 37 | Product Ex. 14 | 20 | 1.5 | — |
| 38 | Product Ex. 15 | 12.5 | 6.0 | 10.1 |
| 39 | Product Ex. 16 | 12.5 | 6.5 | 10.4 |
| 40 | Product Ex. 17 | 12.5 | 8.1 | 6.3 |
| 41 | Product Ex. 18 | 12.5 | 24.0 | 8.6 |
| 42 | Product Ex. 32 | 12.5 | 17.7 | 16.2 |

EXAMPLE 43

The corrosion inhibitor activity of the product of Example 1 is examined in a recirculating pilot cooling water rig system using the standard corrosive water 5M as described in Examples 33 to 36.

The recirculating rig used consists of a 20 liter reservoir of the standard corrosive which is recirculated over two precleaned and preweighed heat exchangers (H1 and H2) and over precleaned and preweighed metal coupons. The reservoir temperature is kept at 40° C. and a high level (80 ppm) inhibitor treatment for one day before continuing with maintenance level (20 ppm) for a further six days.

The heat exchangers and coupons are then cleaned and the corrosion rates are determined in the manner described in Examples 33 to 36. The results are summarised in Table III.

TABLE III

| Example | Inhibitor (80 → 20 ppm) | Corrosion Rate (m.d.d.) | | |
|---|---|---|---|---|
| | | H1 | H2 | coupons |
| — | none (control) | 166.2 | 160.9 | 93.4 |
| 43 | Product Ex. 1 | 5.2 | 12.5 | 2.2 |

EXAMPLES 44 TO 65

The use of the products of this invention, when used in conjunction with other additives, is exemplified by the results shown in Table IV. A product of this invention (COMPONENT A—described in Example 15) is tested in conjunction with a second additive (COMPONENT B) at the dose levels shown. The corresponding result for COMPONENT B in the absence of COMPONENT A is shown for comparison purposes. The test conditions are those of the Rotating Coupon Test described for Examples 37 to 44 above, and all relate to the 150 Ca water.

sion inhibitor efficacy of this material was tested in the D665B rotating spindle test. The result is shown below.

TABLE VI

| Example | Component A | Component B | Dose level of A (ppm) | Dose level of B (ppm) | Corrosion rate (ppm) |
|---|---|---|---|---|---|
| | No additive (control) | | | | |
| | Product of Ex. 15 | — | 7.5 | — | 43 |
| 44 | — | A polyacrylic acid | — | 50 | 33 |
| | Product of Ex. 15 | A polyacrylic acid | 7.5 | 50 | 11.2 |
| 45 | — | A phosphinopolycarboxylic | — | 50 | 60 |
| | Product of Ex. 15 | A phosphinopolycarboxylic | 7.5 | 50 | 7.9 |
| 46 | — | A phosphinopolycarboxylic acid | — | 40 | 43 |
| | Product of Ex. 15 | A phosphinopolycarboxylic acid | 7.5 | 40 | 8.7 |
| 47 | — | A polyacrylic acid | — | 50 | 99 |
| | Product of Ex. 15 | A polyacrylic acid | 7.5 | 50 | 9.1 |
| 48 | — | Phosphate (as o-PO$_4^{2-}$) | — | 5 | 192 |
| | Product of Ex. 15 | Phosphate (as o-PO$_4^{2-}$) | 7.5 | 5 | 11.7 |
| 49 | — | Sodium hexamethaphosphate | — | 20 | 41.6 |
| | Product of Ex. 15 | Sodium hexamethaphosphate | 7.5 | 20 | 17.6 |
| 50 | — | Sodium nitrite | — | 50 | 87 |
| | Product of Ex. 15 | Sodium nitrite | 7.5 | 50 | 5.8 |
| 51 | — | Co-polymer of acrylic acid and acrylamido-propanesulphonic acid | — | 75 | 187 |
| | Product of Ex. 15 | Co-polymer of acrylic acid and acrylamido-propanesulphonic acid | 7.5 | 75 | 96.5 |
| 52 | — | A sulphonated styrene/maleic acid copolymer | — | 50 | 132 |
| | Product of Ex. 15 | A sulphonated styrene/maleic acid copolymer | 7.5 | 50 | 16.5 |
| 53 | — | Zinc | — | 10 | 35 |
| | Product of Ex. 15 | Zinc | 7.5 | 10 | 8.7 |
| 54 | — | Benzoate | — | 100 | 7.5 |
| | Product of Ex. 15 | Benzoate | 7.5 | 100 | 8.5 |
| 55 | — | A triazine carboxylic acid | — | 90 | 70 |
| | Product of Ex. 15 | A triazine carboxylic acid | 7.5 | 90 | 3.9 |
| 56 | — | N-lauroyl sarcosine | — | 20 | 109 |
| | Product of Ex. 15 | N-lauroyl sarcosine | 7.5 | 7.5 | 4.1 |
| 57 | — | HEDP | — | 7.5 | 44 |
| | Product of Ex. 15 | HEDP | 7.5 | 7.5 | 7.2 |
| 58 | — | Molybdate | — | 50 | 90 |
| | Product of Ex. 15 | Molybdate | 7.5 | 50 | 3.9 |
| 59 | — | A polyethyleneoxide derived antifoam | — | 90 | 90 |
| | Product of Ex. 15 | A polyethyleneoxide derived antifoam | 7.5 | 50 | 12.3 |
| 60 | — | A copolymer of acrylic and hydroxymethylacrylic acids | — | 35 | 74.5 |
| | Product of Ex. 15 | A copolymer of acrylic and hydroxymethylacrylic acids | 7.5 | 35 | 9.1 |
| 61 | — | Hydroxyphosphonoacetic acid | — | 5 | 108.7 |
| | Product of Ex. 15 | Hydroxyphosphonoacetic acid | 7.5 | 5 | 7.8 |
| 62 | — | PBSAM | — | 10 | 137 |
| | Product of Ex. 15 | PBSAM | 7.5 | 7.5 | 12.8 |
| 63 | — | A polymaleic acid | — | 20 | 70.3 |
| | Product of Ex. 15 | A polymaleic acid | 7.5 | 20 | 31.9 |
| 64 | — | Tolutriazole | — | 75 | 151.0 |
| | Product of Ex. 15 | Tolutriazole | 7.5 | 75 | 19.3 |
| 65 | — | A tetraalkylphosphonium salt | — | 10 | 131 |
| | Product of Ex. 15 | A tetraalkylphosphonium salt | 7.5 | 10 | 15.8 |
| 66 | — | A polymaleic based polymer | — | 20 | 151 |
| | Product of Ex. 15 | A polymaleic based polymer | 7.5 | 20 | 21.6 |

EXAMPLE 67

As an Example of a further use of compounds in this invention, the product of Example 15, in its cyclised form (that is, as shown by formula II) was dissolved in a mineral oil to produce a 200 ppm solution. The corro-

| Additive level | Degree of Corrosion |
|---|---|
| 0 (blank) | Severe |

-continued

| Additive level | Degree of Corrosion |
|---|---|
| 2000 ppm | No rust |

We claim:

1. A process for inhibiting the corrosion of a metal surface comprising: contacting the metal surface with a composition comprising:
   a) an aqueous-based system; and
   b) as an inhibitor for protecting the metal surface against corrosion, at least one compound having the formula I or II:

$$R(OCH_2)_a CHCH_2(OCH-CH)_b O(CH)_c CO_2 M \quad \text{I}$$
$$\text{with substituents } OH, R^1, R^2, R^3$$

or

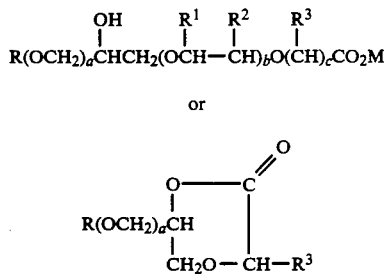

II in which
R is $C_4$–$C_{20}$alkyl, $C_4$–$C_{20}$alkyl interrupted by one or more oxygen atoms, $C_4$–$C_{20}$alkenyl, $C_6$–$C_{20}$aryl, $C_7$–$C_{15}$alkaryl, $C_7$–$C_{15}$aralkyl or $C_5$–$C_{12}$cycloalkyl;

$R^1$, $R^2$ and $R^3$ are the same or different and each is methyl or hydrogen;

M is hydrogen, a metal ion, ammonium or substituted ammonium ion;

a is 0 or 1;

b is 0 or an integer from 1 to 6; and c is an integer from 1 to 6.

2. A process according to claim 1 in which the metal surface is a ferrous metal surface.

3. A process according to claim 1 in which $R^1$, $R^2$ and $R^3$ are hydrogen.

4. A process according to claim 1 in which b is 0, 1, 2 or 3.

5. A process according to claim 4 in which b is 0 or 1.

6. A process according to claim 1 in which c is 1, 2 or 3.

7. A process according to claim 1, wherein R is of straight-chain and has 6 to 16 carbon atoms.

8. A process according to claim 7, wherein R is of straight-chain and has 8 to 15 carbon atoms.

9. A process according to claim 8, wherein R is of straight-chain and has 12 to 15 carbon atoms.

10. A process according to claim 1, in which R is $C_6$–$C_{16}$alkyl, a is 0 or b is 0, 1, 1, 2 b is 0, 1, or 3 and c is 1, 2 or 3.

11. A process according to claim 10 in which R is $C_8$–$C_{15}$alkyl, a is 0 or 1, b is 0 or 1 and c is 1, 2 or 3.

12. A process according to claim 11, wherein R is $C_{13}$–$C_{15}$alkyl, a is 1, b is 0 and c is 1.

13. A process according to claim 1 in which M is hydrogen, sodium or potassium, magnesium or calcium, bis(2-hydroxyethyl)ammonium, tris(2-hydroxyethyl)ammonium or bis(2-hydroxyethyl)-(2-hydroxy-3-p-nonylphenoxy)propylammonium.

14. A process according to claim 1, wherein the amount of the compound of formula I or II present is 0.0001 to 5% by weight, based on the total amount of the aqueous-based system.

15. A process according to claim 1 further comprising one or more antioxidants, metal deactivators, corrosion inhibitors, rust inhibitors, complexing agents, precipitation inhibitors, biocides, buffering agents or antifoams.

16. A process according to claim 1 wherein the compound of formula I or II has been produced by reacting a diol of the formula VI:

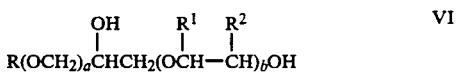

with an ω-halocarboxylic ester of the formula VII:

to obtain a compound of formula VIII:

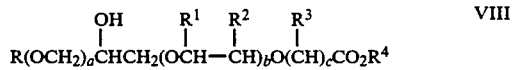

and/or a compound of formula X

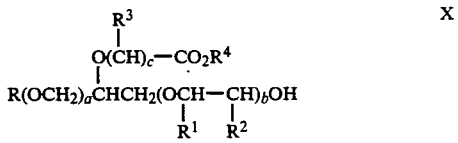

wherein
R is $C_4$–$C_{20}$alkyl, $C_4$–$C_{20}$alkyl interrupted by one or more oxygen atoms, $C_4$–$C_{20}$alkenyl, $C_6$–$C_{10}$aryl, $C_7$–$C_{15}$alkaryl, $C_7$–$C_{15}$aralkyl or $C_5$–$C_{12}$cycloalkyl;

$R^1$, $R^2$ and $R^3$ are the same or different and each is methyl or hydrogen;

M is hydrogen, metal ion, ammonium or substituted ammonium ion;

a is 0 or 1;

b is 0 or an integer from 1 to 6; and c is an integer from 1 to 6

X is a halogen and $R^4$ is a hydrocarbon residue and hydrolyzing the compound of formula VIII and/or X, to produce the corresponding compound of the formula I or II.

17. A process according to claim 1 wherein the compound of formula I or II has been produced by reacting a diol of the formula VI:

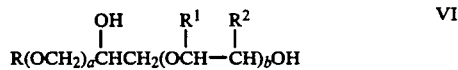

with an ω-halo acid or salt of formula IX:

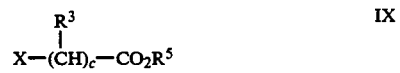

in the presence of an appropriate amount of base, to produce a compound of formula I or II directly, or in combination with a compound of formula XI:

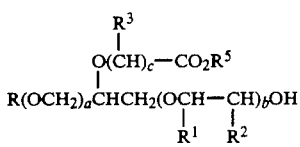

wherein
- R is $C_4$-$C_{20}$alkyl, $C_4$-$C_{20}$alkyl interrupted by one or more oxygen atoms, $C_4$-$C_{20}$alkenyl, $C_6$-$C_{18}$aryl, $C_7$-$C_{15}$alkaryl, $C_7$-$C_{15}$aralkyl or $C_5$-$C_{12}$cycloalkyl;
- $R^1$, $R^2$ and $R^3$ are the same or different and each is methyl or hydrogen;
- M is hydrogen, metal ion, ammonium or substituted ammonium ion;
- a is 0 or 1;
- b is 0 or an integer from 1 to 6; and
- c is an interger from 1 to 6
- X is a halogen and
- $R^5$ is hydrogen or a metal ion, 18. A process according to claim 1 wherein the compound of formula I in which $R^3$ is H and c is 2 has been obtained by reacting a diol of the formula VI:

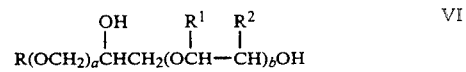

with acrylic acid or its sodium salt, in the presence of an appropriate amount of base, wherein
- R is $C_4$-$C_{20}$alkyl, $C_4$-$C_{20}$alkyl interrupted by one or more oxygen atoms, $C_4$-$C_{20}$alkenyl, $C_6$-$C_{10}$aryl, $C_7$-$C_{15}$alkaryl, $C_7$-$C_{15}$aralkyl or $C_5$-$C_{12}$cycloalkyl;
- $R^1$ and $R^2$ are the same or different and each is methyl or hydrogen;
- a is 0 or 1;
- b is 0 or an integer from 1 to 6.

19. A process according to claim 1 wherein component b) is the inhibitor of formula II.

* * * * *